(12) United States Patent
Carey

(10) Patent No.: US 11,793,785 B2
(45) Date of Patent: Oct. 24, 2023

(54) THIN FILM OXIDATION OF CRYSTALLIZED CANNABIS PRODUCTS

(71) Applicant: Vapor Oil Technology LLC, Jackson, MI (US)

(72) Inventor: Chad Arthur Carey, Pheonix, AZ (US)

(73) Assignee: Vapor Oil Technology LLC, Jackson, MI (US)

( * ) Notice: Subject to any disclaimer, the term of this patent is extended or adjusted under 35 U.S.C. 154(b) by 0 days.

(21) Appl. No.: 17/960,682

(22) Filed: Oct. 5, 2022

(65) Prior Publication Data

US 2023/0040806 A1  Feb. 9, 2023

(51) Int. Cl.
*A61K 31/352* (2006.01)
*A61K 36/185* (2006.01)

(52) U.S. Cl.
CPC .......... *A61K 31/352* (2013.01); *A61K 36/185* (2013.01); *A61K 2236/35* (2013.01); *A61K 2236/53* (2013.01); *A61K 2236/55* (2013.01)

(58) Field of Classification Search
CPC .............. A61K 31/352; A61K 2236/35; A61K 2236/53; A61K 2236/55
See application file for complete search history.

(56) References Cited

U.S. PATENT DOCUMENTS

| | | | |
|---|---|---|---|
| 8,192,589 B2 * | 6/2012 | Winkelaar | ............... C07C 51/44 562/580 |
| 2021/0251157 A1 * | 8/2021 | Leo | ......... B01D 9/004 |
| 2023/0083465 A1 * | 3/2023 | Carey | ................. A61K 31/015 424/725 |

* cited by examiner

*Primary Examiner* — Sikarl A Witherspoon
(74) *Attorney, Agent, or Firm* — Kevin H. Fortin, Esq.

(57) ABSTRACT

Crystallized cannabis extract having a purple color is made by first providing cannabis having a detectable amounts of tetrahydrocannabinolic acid (THCA) as well as secondary components including terpenes. Pentane or other solvent is added to the cannabis material to dissolve the secondary components. The cannabis material is enclosed in a filter basket, or a rosin press filter bag, having an average pore diameter of 25 microns. The centrifuge spins the filter bag or filter basket to separate the THCA from the cannabis material and thereby yielding a primary product that is a concentrated cannabis material having at least 95% THCA and a secondary product (high terpene extract) having combined THCA and secondary components including terpenes. The concentrated cannabis material is distilled in a wiped film evaporator or a short path evaporator to oxidize the concentrated cannabis material and yield a super concentrated cannabis material having at least 98% THC.

22 Claims, 3 Drawing Sheets

THIN FILM OXIDATION OF CRYSTALLIZED CANNABIS PRODUCTS

FIELD OF THE INVENTION

The present invention relates to more efficient ways of purifying and naturally coloring cannabis concentrate and distillate, more particularly this invention relates to producing a colored and tinted cannabis product through the process of thin film oxidation.

BACKGROUND OF THE INVENTION

The term "THC" usually refers to the trans-$\Delta^9$-tetrahydrocannabinol, which is a $\Delta^9$ isomer. The term "THC crystals", is often a misnomer. While THC can be formed into a glass-like sheet called shatter, or a distillate powder, it does not naturally crystallize under most conditions.

Tetrahydrocannabinolic acid "THCA" can naturally crystallize when in a concentrated solution. In ideal conditions THCA crystals naturally form. Some believe that it is easier under most circumstances to use crystallization to concentrate THCA than it is to concentrate THC.

THCA has two major isomers, THCA-A, in which the carboxylic acid group is in the 1 position, between the hydroxy group and the carbon chain, and THCA-B, in which the carboxylic acid group is in the 3 position, following the carbon chain. Both isomers, when crystallized, typically have a colorless appearance. The terms "tetrahydrocannabinolic acid", and "THCA", as used herein includes both of these isomers.

Many customers of cannabis products believe that naturally occurring components are desirable and additives and adjuncts are less desirable. This is especially true for smokable products. It can be generalized that customers like natural products because there is less perceived risk of toxicity.

THCA products have become more popular. Some provide the interesting inclusion of crystals, which are aesthetically pleasing. THCA, however, is not normally psychoactive when consumed orally. It must be heated or smoked to convert it into THC to yield psychoactive effects.

Common ways to make crystallized THCA includes the use of a rosin press to separate THCA from terpenes, waxes, chlorophyll, and other components. Repeated mechanical pressing can achieve a pure white crystal having 95-99% purity. Rosin presses sometimes use hydraulic plates that sequentially squeeze rosin press filter bags having incrementally smaller pore sizes to extract THCA from cannabis.

Alternatively some use a diamond miner to produce THCA crystals. "Diamond mining" refers to the process of crystallizing THCA from a cannabinoid and terpene-rich oil. If done properly, some of the THCA present will crystallize and drop out of the solution. Cannabinoid and terpene-rich viscous fluid, sometimes termed a high terpene extract (HTE) can be poured off leaving the THCA crystals. This process is typically done in the presence of a hydrocarbon extract to separate the THCA and relies on light heat and pressure to facilitate crystallization.

Another alternative includes a solvent-based method requiring mixing cannabis extract with solvents like acetic acid (purified vinegar) or a hydrocarbon. Next, chromatography and a rotary evaporator are used to concentrate the THCA.

U.S. Pat. No. 8,192,589B2 to Winkelaar et al. is an example of an effective short path evaporator for vacuum distillation. This evaporator purifies an aqueous solution of an organic acid having a boiling point at atmospheric pressure of less than 450° C. According to the method, this solution is subjected to two or more distillation steps, the first distillation step being carried out at a temperature of from 80° to 150° C. and a pressure of from 50 to 250 mbar, and the second distillation step being carried out at a temperature of from 80° to 200° C. and a pressure of from 0.01 to 50 mbar. Similar systems enable precise temperatures and pressures, along with mechanical blade movement to isolate and concentrate cannabinoids. However, operating this equipment requires both energy and time. It may not be the most efficient system.

While the Winkelaar et al. invention is certainly useful, employing two distillation steps is time and energy consuming. What is desired is a more efficient way of processing material. What is also desired is a way of processing cannabis material that naturally colors the processed material without dyes, pigments, or synthetic chemicals.

SUMMARY OF THE INVENTION

The present invention includes utilizing two primary steps to yield a concentrated THC cannabis product that is purple in color without the use of dyes or additives. This THC cannabis concentrate product can be modified in various post processing steps to make shatter or distillate having aroma and flavor, without additives not found in the original cannabis material used for the process. Various consumer products can be manufactured using the post processed THC product, which typically is purple in color, having at least 90% THC content. Such consumer products may be engineered to have a desirable flavor and aroma. The form of this concentrated THC product can be a glass-like shatter product or packaged distillate, for example. More preferably the consumer products have a greater than 95% THC content.

The first step is to use a centrifuge to achieve THCA separation. Optimally this is accomplished by centrifuging rosin press filter bags of cannabis material and including a suitable solvent such as pentane or hexane. In various alternate embodiments, the filter bags are replaced with stainless steel baskets or other shape 20-30 micron filters. Preferably the filter has an average of 25 micron pore diameter size in all embodiments.

The pentane partially, or fully saturates, the cannabis material. Preferably the cannabis material is full spectrum cannabis oil having at least 60% THCA content. The filter bags have pores with an average diameter of 25 microns to retain THCA within the bags during the centrifuge process. This concentrates the THCA to over 95% purity, and often over 98% purity, yielding a first concentrated THCA product. This is a very fast an efficient way to achieve a concentrated THCA product.

The first step also yields a wash bi-product including THCA, terpenes and pentane solvent, which are recoverable using conventional processes such as high pressure liquid chromatography, ethanol distillation, or a mechanical means such as a centrifuge.

Both the first concentrated THCA product and THCA can be recovered from the wash bi-product and decarboxylated into a viscous liquid having at least 95% THC concentration.

Alternatively, the wash bi-product can be lightly purged and then introduced to other products. It is possible to extract pure terpenes from the wash bi-product, and these pure terpenes can be selectively mixed with a purple shatter product in accord with the present invention to add flavor and aroma, without degrading the integrity of the purple shatter product either in texture, hardness and color. In a preferred embodiment, the pure terpenes constitute no more than 1-2% of the shatter product.

In an alternate embodiment the wash bi-product can be introduced into a purple THC product used as vaporizable oil, packaged for use in a vaporizer cartridge, or packaged in a vaporizer cartridge. In this embodiment, the terpene level can be up to 10%. Optimally, the product packaged for and used in a vaporizer cartridge has a THC concentration between 95%-99%.

The second step is to introduce the decarboxylated THC product into a wiped film evaporator, which is technically a short path evaporator that uses a thin film and a mechanical blade to speed the process of distillation/evaporation. The wiped film evaporator is primarily used to oxidize the concentrated THC product. This transforms the concentrated THC product on a continuous basis into a thin film that is wiped by a rotating blade to rapidly oxidize the concentrated THC product and thereby yield an oxidized THC product that is purple in color.

In an alternate embodiment of the product of the invention, various terpenes are mixed into the oxidized THC product to provide aroma and flavor. These various terpenes typically do not arise to more than 1-2% of the terpene-infused alternate product.

In yet another alternate embodiment, the oxidized THC product is processed again in the wiped film evaporator to achieve an above 99% purity and to assure optimal oxidation. This step may repeat.

In a variation of the step of using the centrifuge, the cannabis material is saturated by dripping pentane onto it and bagging the saturated cannabis material in a filter bag having a 25 micron pore size, a stainless steel basket having 25 micron pore sizes, or other filter. The step of centrifuging the saturated cannabis material whisks a wash bi-product from the cannabis material out of the filter bag via the 25 micron pores. This wash bi-product is a high terpene extract (HTE) and contains some THCA along with terpenes, which are both recoverable.

Manufacturing Efficiency Improvement

The centrifuged THCA product is provide quickly and may immediately yield over half of the THCA available, in a pure form. In parallel, the high terpene extract (HTE) byproduct can be conventionally processed to yield THCA. The HTE byproduct also includes terpenes and residual pentane that can be processed conventionally. Thus both methods are utilized in parallel. The amount of material conventionally processed is halved to achieve manufacturing efficiency.

Recovery of THCA from the HTE entails removing or evaporating the pentane and re-dissolving the dry HTE in butane. This enables the THA-A to crystallize in the butane rich environment.

In another embodiment, the recovery of THCA from the HTE entails placing the HTE into a sealed container such as a jar, and spinning the container of the HTE in the centrifuge. Removing the jar enables formation of pure THCA crystals over time to improve yield of the THCA product.

Simply stated, a number of ways are used to process the wash bi-product to re-crystallize and to recover THCA that was not initially recovered in the filter bag. An advantage of stems from the fact that that the bi-product wash can be speedily processed via conventional and mechanical means while the wiped film evaporator runs. This manufacturing efficiency utilizes parallel processes at the same time to more rapidly product concentrated cannabis products. It is estimated that the parallel processing the THCA using a centrifuge and the HTE processing at the same time cuts product time in half, or stated differently increases production capacity by 2x, with a greater efficiency in terms of yield. More terpenes are preserved when separated and purged at lower temps such as the mechanical processing (centrifuge) enables. Mechanical processing at lower temperatures (below the decarboxylation temperature of THCA) also maintains the integrity of the THCA so that it can be most efficiently separated or extracted.

In one embodiment the step of re-capturing using butane is at room temperature and after saturation allows the butane to evaporate in a vented room as the evaporative process cools the mixture allowing the THCA to form crystals. This process can take less than 24 hours. The HTE byproduct yields 10%-90% THCA in the form of white crystals and requires a minimum of mechanical equipment, space and energy. These THCA crystals can then be fully decarboxilated into THC.

The THC is then oxidized by heating in a wiped film evaporator to achieve a purified and purple colored product. The HTE byproduct can also be further processed to extract terpenes that can be added back to the purified and purple colored product to add flavor and aroma.

Variations of Decarboxylation Timing

Decarboxylation of the THCA can occur prior to processing in the wiped film evaporator, can occur while in the wiped film evaporator, or after the wiped film evaporator processes the concentrated cannabis material.

Heat hastens decarboxylation and also oxidation. 95%+ THC can be kept as a viscous liquid having a very light yellow color. This viscous liquid is spread thin in wiped film evaporator to oxidize and pull non-THC components out, yielding an oxidized, decarboxilated and highly purified THC having at least a 90% THC concentration, and preferably 98-99% THC concentration. Natural oxidation occurs to the highly purified THC due to thin sheet geometry, which maximizes surface area exposed to ambient oxygen. This oxidation turns the highly purified THC purple in color naturally without dies or additives. In one embodiment oxygen is introduced into the wiped film evaporator to more rapidly oxidize the THC. In this embodiment, less heat is required. In an alternate embodiment a reactive oxygen species is introduced such as superoxide.

In a post process, terpenes are added to the highly purified THC that is purple in color to yield shatter having a greater than 95% THC concentration. The purple color is retained. Simply stated, removing terpenes destabilizes THC to enable it to oxidize and turn purple, then terpenes can be added back to provide aroma and flavor. Grinding the shatter makes a purple colored crystallized distillate product that can be packaged in a jar.

In another post process, the crystallized purple distillate product is used to make beverages, gummies, candies, and other edible product. Since the distillate product is highly concentrated, this post process may include adding anthocyanins to optimize color. The anthocyanins can be produced from powdered fruit, for example, by saturating with pentane in a filter bag and centrifuging to yield a purified anthocyanin. Blueberry powder, for example, can be used to yield a blue anthocyanin food grade dye that can be added to post process products to enhance color. In an alternate embodiment, beet root can be processed in a manner similar to anthocyanin to yield betalains that can be used as a post process food grade natural dye.

DETAILED DESCRIPTION

The present invention relies upon a centrifuge to rotate cannabis material in nylon rosin filter bags having a 25 micron average pore size. A C1D2 model centrifuge such as sold by C1D1 Labs having a 100 gallon capacity, or other capacity, can be used in accordance with the present invention.

In one embodiment the cannabis material is extracted cannabis oil having a THCA content and secondary material including terpenes. The centrifuge separates the secondary materials from the tetrahydrocannabinolic acid from to yield a concentrated cannabis material having at least 95% tetrahydrocannabinolic acid (THCA), and preferably 98-99% THCA. This THCA is decarboxylated and transferred into a wiped film evaporator for oxidation and, in various embodiments, additional decarboxylation.

Figure 1:
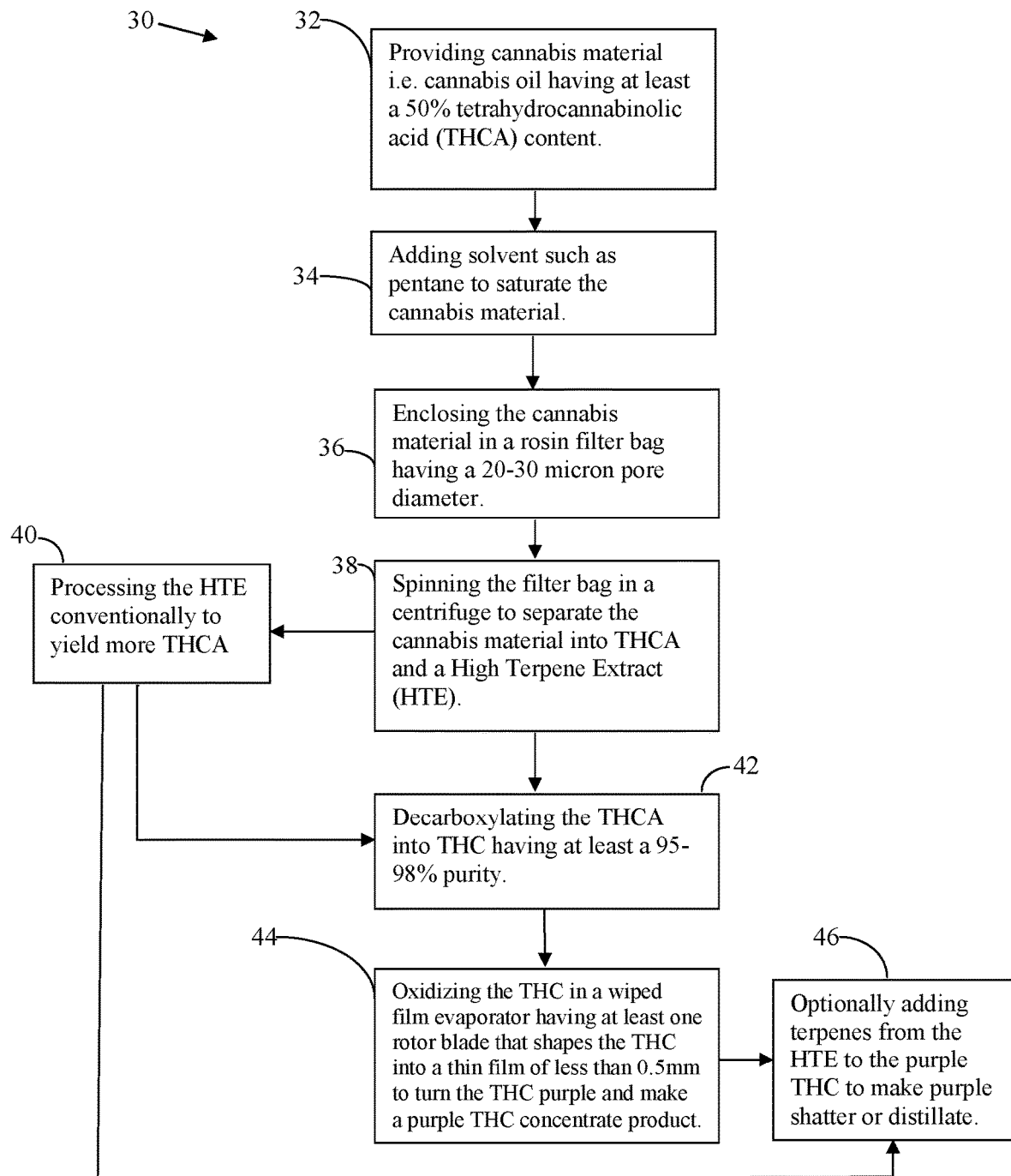
FIG. 1 is a flow chart for using a wiped film evaporator to purify and oxidize THC into a purple color.

FIG. 1 is a flow chart describing a method 30 of efficiently manufacturing a concentrated and decarboxilated THC product that is purple in color, and has at least 98% THC content. This concentrated product can be mixed with cannabis terpenes to add flavor and aroma. Various consumer products can be made with this concentrated product including shatter and distillate that is packaged in ajar.

The method 30 includes the step 32 of providing cannabis material. In one embodiment, the cannabis material can be full spectrum cannabis oil, typically having at least a 50% THCA content. It can have any amount of THCA, but using oil with at least 50%, and preferably at least 60% is more efficient than using cannabis material having a lesser concentration of THCA.

The step 34 follows and solvent is added to the cannabis material to separate the THCA. The solvent can be selected from the group consisting of acetic acid, other acid, ethanol, other alcohols, hydrocarbons, pentane, hexane, butane or other solvent. Preferably pentane is used because it is relatively non-toxic, readily available, rapidly effective, and relatively inexpensive. The pentane partially saturates, or fully saturates, the cannabis material. Preferably the pentane is dripped onto the cannabis material.

The step 36 encloses the cannabis material in a rosin filter bag having a 20-30 micron pore diameter, or alternatively a stainless steel basket having a similar pore diameter. This step 36 can come prior to the step 34 of adding solvent, or afterwards. Preferably, the rosin filter bag has an average pore diameter of 25 microns+/−1 micron. The filter bags are typically made from nylon, or other polymer capable of resisting solvent and heat of at least 300° F. These rosin filter bags are used because they are widely available for rosin press users, and are inexpensive. The present invention includes the discovery that these rosin press bags are suitable for use in a centrifuge, and while not super efficient, can greatly increase efficiency of select manufacturing processes that produce purified and oxidized THC products.

The filter bag is spun in the step 38 in a centrifuge to separate the cannabis material into pure (<95%) THCA and a High Terpene Extract (HTE). Preferably the THCA is purified to greater than 98%.

The step 40 processes the HTE conventionally to yield more THCA. The HTE includes THCA, terpenes, and solvent (pentane) so removing of the solvent can enable isolation and separation of this additional THCA, and the particular terpenes. High Pressure Liquid Chromatography (HPLC), vacuum distillation in a rotating vaporizer, or processes, for example, can remove and isolate the particular terpenes and the THCA.

In one embodiment, the step 40 is modified to be novel and unconventional. Pentane from the HTE is removed. The HTE is saturated with butane. The butane and HTE mixture can be shelved for 24 hours to allow the butane to evaporate at standard temperature and pressure, leaving THCA crystals and terpenes. Both the THCA and terpenes can be used in accord with the present invention is post process steps. The THCA can be mixed with the THCA removed from the rosin filter bag and both can be decarboxilated as per step 42 into THC having at least 95-98% concentration, or greater concentration, and next fed to a wiped film evaporator, or short path distillation device, or similar device, to enable oxidation of the THC to purify the THC and turn the THC purple.

The step 44 oxidizes the THC in a wiped film evaporator having at least one rotor blade that shapes the THC into a thin film of less than 0.5 mm to turn the THC purple and make a purple THC concentrate product. While a thin film is used to process the THC, rolled films and other methods may be applicable to generate the purple color and optimally concentrate the THC to above 98% purity.

The step 46 optionally adds terpenes from the HTE to the purple THC to make a purple distillate or shatter product having desired aroma and flavor, and a THC purity of between 95% and 98%.

All purities and concentrations expressed herein are on a weight to weight (w:w) basis. The filter basket or filter bag can include any shape or suitable material having an approximately 25 micron pore diameter for use in the centrifuge. While the present invention is described by way of example only, the detailed scope of the invention is set forth in the appended claims.

Figure 2:
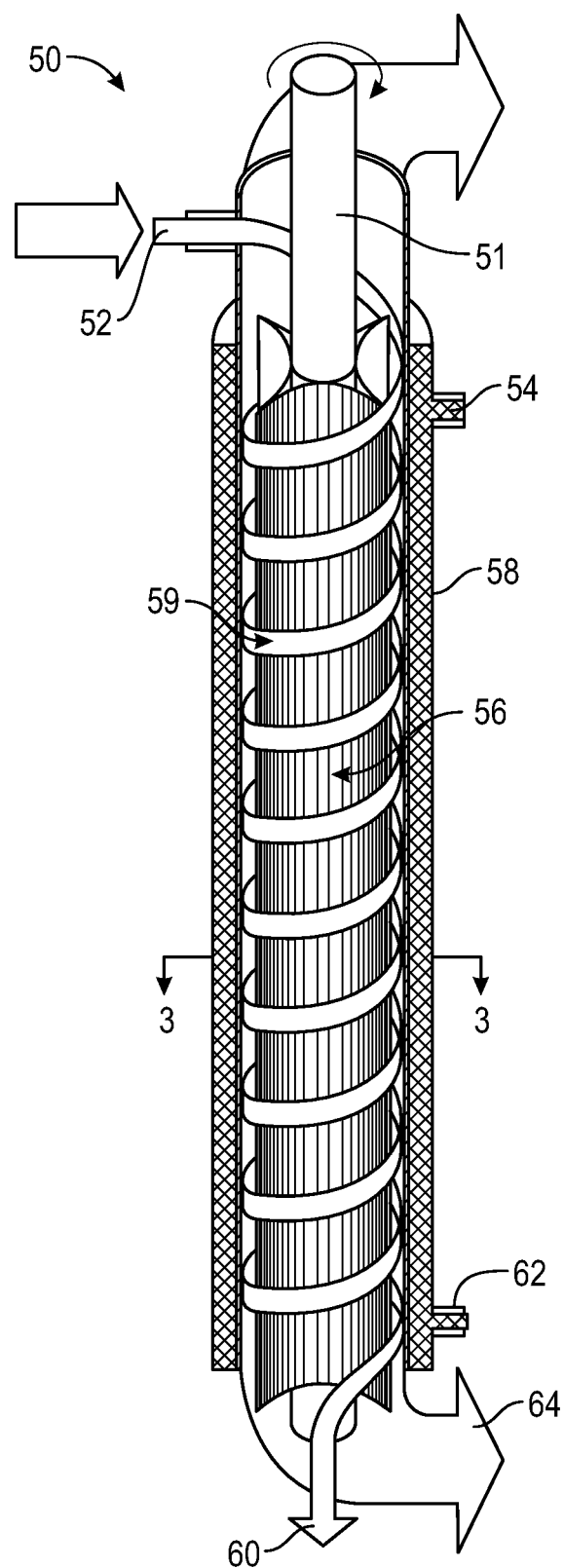
FIG. 2 is an example of the wiped film evaporator.

FIG. 2 is a Wiped Film Evaporator (WFE) generally designated with the reference numeral 50. The WFE includes a rotatable shaft 51, a feed port 52, a heating input port 54 a rotor 56 connected with the shaft 51 that rotates a plurality of aligned auger blades aligned with an axis of the shaft 51, a shell 58, a product exhaust port 60, a heating fluid output port 62. In variations of the WFE 50, the WFE includes a vacuum port, residue port, cooling water ports and a vapor exhaust port 64.

The wiped film evaporator (WFE) 50 is a piece of commercially available equipment normally used for concentration, distilling, stripping, dehydration and deodorization of products which are heat sensitive or viscous. The equipment can handle a very wide range of feed compositions ranging from 1% to over 98% THC concentrations.

In accord with the present invention, the WFE 50 has several advantages and newly discovered unique functions for thin film oxidation of THC to yield a purple THC product. The operation is continuous. Continuous contact wipers or blades 56 produce and renew the thin film, whose thickness effects any rate of oxidation. Such an operation improves product yield while enabling oxidation of the cannabis material having at least 95% THC, and preferably greater than 98% THC.

The operation process in the WFE 50 is simple but yet effective. Feed material i.e. THC is introduced at the top of the unit an passes in a helical direction 59 to form a thin film that spreads on the shell 58 inner surface in response to the shaft 51 rotation. Specially designed wipers or blades 56 wipe the feed material thus creating and renewing the film. This thin film enables an efficient heat transfer and oxidation. The non-THC components having a relatively lower boiling point evaporate and pass through an entrainment separator. These non-THC components are removed through the vapor exhaust port 64. In one embodiment oxygen is fed through the feed port 52 along with THC to enhance the oxidation of the thin film.

The THC is transferred out through the distillate port in a concentration of at least 98%. Importantly the WFE uses a rotating bladed system to wipe a layer of film with each pass to enable oxidation of the THCA that is exposed to ambient oxygen at controlled temperatures and pressures. The THCA is further concentrated in one embodiment to nearly 99% purity and at this purity the THCA readily changes color to purple under appropriate environmental conditions at which the WFE device is controlled to operate.

Figure 3:
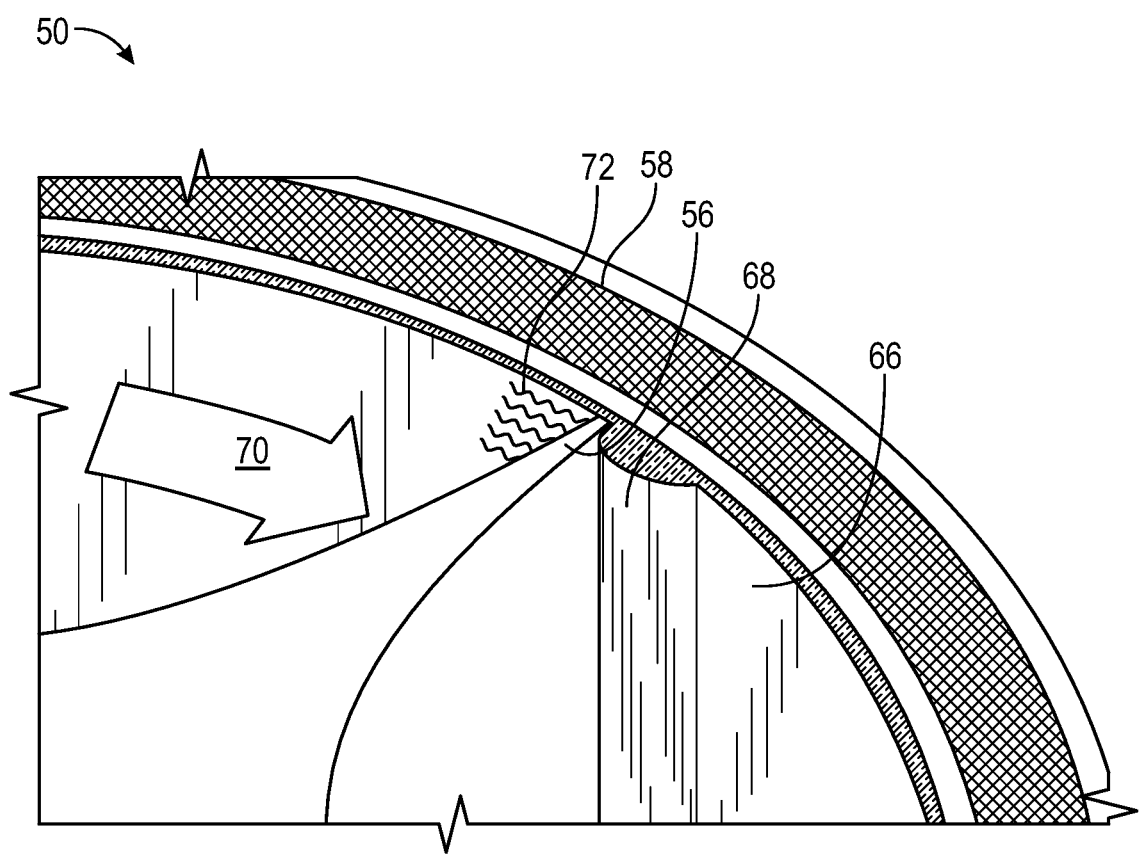
FIG. 3 is a partial sectional view of the rotor blade of the wiped film evaporator of FIG. 2 as seen along the line 3-3.

FIG. 3 shows the operation of the WFE 50. It includes the shell 58 having a cylindrical interior coated with THC 66. The WFE50 includes a rotatable blade 56 that skims the THC 66 under suitable temperature and pressure to create a bow wave 68, and yield a thin film 72 behind the blade 56 opposing the bow wave 68. The wiped thin film material is sent via the outlet 60 of the WFE 50 in FIG. 2 as super concentrated cannabis material having a THC concentration of at least 95%, and preferably at least 98%.

While a commercially available WFE is shown by way of example, many devices can achieve optimal distillation of the cannabis material having THC in high concentrations such as above 98% to oxidize the cannabis material and change the color to purple. While the present invention is described in terms of delta-9 tetrahydrocannabinol, the present invention can also be used in the production of other isomers including delta-8 tetrahydrocannabinol having a purple color. The present invention further includes products manufactured with the processes and methods of the present invention.

The WFE maintains sufficient heat and in-situ time to decarboxylate any residual THCA into THC to yield a concentrated THC product, which can be used in orally deliverable products such as edibles, oils, and candies or gummies. The THC product can also be formulated into a vapor oil product that maintains a purple color during its shelf life.

I claim:

1. A method for manufacturing delta-9 tetrahydrocannabinol having a purple color comprising:
    a. providing cannabis material having a detectable tetrahydrocannabinolic acid (THCA) content;
    b. adding a solvent to the cannabis material;
    c. enclosing the cannabis material in a filter bag, the filter bag having a pore diameter of between 20-30 microns;
    d. spinning the filter bag in a centrifuge to separate the cannabis material into tetrahydrocannabinolic acid (THCA) and a high terpene extract (HTE);
    e. the step of spinning yields tetrahydrocannabinolic acid having at least a 95% purity;
    f. decarboxylating the tetrahydrocannabinolic acid into delta-9 tetrahydrocannabinol (THC); and
    g. oxidizing the delta-9 tetrahydrocannabinol in a wiped film evaporator having at least one rotor blade that shapes the delta-9 tetrahydrocannabinol into a thin film to turn it purple.

2. The method as set forth in claim 1, wherein the solvent is at least 90% pentane.

3. The method as set forth in claim 1, wherein the cannabis material is full spectrum cannabis oil and has at least a 50% THCA content, the filter bag is a nylon rosin filter bag having an average pore diameter of 25 microns within a margin of variability of +/−5%.

4. The method as set forth in claim 2, wherein the solvent is at least 99% pentane.

5. The method as set forth in claim 1, wherein the solvent is at least 90% hexane.

6. The method as set forth in claim 1, wherein the solvent includes a mixture of pentane and hexane.

7. A method for manufacturing a cannabis extract having a purple color comprising:
    a. providing cannabis material having tetrahydrocannabinolic acid (THCA), and secondary components including terpenes;
    b. adding pentane to the cannabis material to dissolve the secondary components;
    c. enclosing the cannabis material in a filter means, the filter means having an average pore diameter of 25 microns;
    d. spinning the filter means in a centrifuge to separate the tetrahydrocannabinolic acid from the cannabis material, to yield a concentrated cannabis material having at least 95% tetrahydrocannabinolic acid;
    e. distilling the concentrated cannabis material in a wiped film evaporator or a short path evaporator to oxidize the concentrated cannabis material and yield a super concentrated cannabis material having at least 98% delta-9 tetrahydrocannabinol (THC).

8. The method as set forth in claim 7, wherein the step of distilling employs a wiped film evaporator that rotates a rotor blade along a heated wall to generate a turbulent liquid film layer and a liquid film bow wave to create optimal heat flux conditions to separate volatile components from the cannabis material and to yield a super concentrated cannabis material.

9. The method as set forth in claim 8, wherein the wiped film evaporator decarboxylates the cannabis concentrate and yields a decarboxylated super concentrated cannabis material having at least 98% delta-9 tetrahydrocannabinol.

10. The method as set forth in claim 9, wherein the super concentrated cannabis material has at least 99% delta-9 tetrahydrocannabinol.

11. The method as set forth in claim 10, wherein the super concentrated cannabis material is formed in a flat sheet to create a stabilized shatter product.

12. The method as set forth in claim 10, wherein the super concentrated cannabis material is crushed into granules and packaged in a glass jar to create a stabilized distillate product.

13. The method as set forth in claim 12, wherein the super concentrated cannabis material is crushed into granules having an average diameter of less than 1 mm and packaged in a glass jar to create a stabilized distillate product.

14. A method for manufacturing a crystallized cannabis extract having a purple color comprising:
    a. providing cannabis material having a detectable amount of tetrahydrocannabinolic acid (THCA), and having secondary components including terpenes;
    b. adding pentane to the cannabis material to dissolve the secondary components;
    c. enclosing the cannabis material in a filter basket, the filter basket having an average pore diameter of 25 microns;
    d. spinning the filter basket in a centrifuge to separate the tetrahydrocannabinolic acid from the cannabis material, to yield a primary product that is a concentrated cannabis material having at least 95% tetrahydrocannabinolic acid and a secondary product having combined tetrahydrocannabinolic acid and secondary components including terpenes;

e. distilling the concentrated cannabis material in a wiped film evaporator or a short path evaporator to oxidize the concentrated cannabis material and yield a super concentrated cannabis material having at least 98% delta-9 tetrahydrocannabinol; and f. mixing a fraction of the secondary product terpenes into the super concentrated cannabis material.

15. The method as set forth in claim 14, wherein the step of distilling employs a wiped film evaporator that rotates a rotor blade along a heated wall to generate a turbulent liquid film layer and a liquid film bow wave to create optimal heat flux conditions to separate volatile components from the cannabis material.

16. The method as set forth in claim 15, wherein the wiped film evaporator decarboxylates the cannabis concentrate and yields a concentrated delta-9 tetrahydrocannabinol cannabis material having at least 98% delta-9 tetrahydrocannabinol.

17. The method as set forth in claim 16, wherein the super concentrated cannabis material has at least 99% delta-9 tetrahydrocannabinol.

18. The method as set forth in claim 14, wherein the super concentrated cannabis material is formed in a flat sheet to create a stabilized shatter product.

19. The method as set forth in claim 14, wherein the super concentrated cannabis material is crushed into granules and packaged in a glass jar to create a stabilized distillate product.

20. The method as set forth in claim 19, wherein the super concentrated cannabis material is crushed into granules having an average diameter of less than 1 mm and packaged in a glass jar to create a stabilized distillate product.

21. The method as set forth in claim 20, further comprising adding butane to the secondary product to extract THCA from the secondary product.

22. The method as set forth in claim 20, further comprising packaging the secondary product in ajar, centrifuging the jar and allowing the jar to sit until THCA forms crystals from secondary product.

\* \* \* \* \*